US 7,999,123 B2

(12) United States Patent
Urata et al.

(10) Patent No.: US 7,999,123 B2
(45) Date of Patent: Aug. 16, 2011

(54) 2-OXETANONE DERIVATIVE AND PROCESS FOR PRODUCTION THEREOF

(75) Inventors: Yasuo Urata, Chiba (JP); Shunji Oshima, Kumamoto (JP); Ryousuke Nishibata, Kumamoto (JP); Keiichi Kodaki, Kumamoto (JP); Hiroyuki Takeuchi, Chiba (JP); Shuichi Matsui, Chiba (JP)

(73) Assignees: JNC Corporation, Tokyo (JP); Chisso Petrochemical Corporation, Tokyo (JP)

( * ) Notice: Subject to any disclaimer, the term of this patent is extended or adjusted under 35 U.S.C. 154(b) by 131 days.

(21) Appl. No.: 12/301,605

(22) PCT Filed: May 17, 2007

(86) PCT No.: PCT/JP2007/060147
§ 371 (c)(1),
(2), (4) Date: Nov. 19, 2008

(87) PCT Pub. No.: WO2007/135954
PCT Pub. Date: Nov. 29, 2007

(65) Prior Publication Data
US 2009/0275756 A1  Nov. 5, 2009

(30) Foreign Application Priority Data

May 23, 2006  (JP) ................................. 2006-142934

(51) Int. Cl.
*C07D 305/12* (2006.01)
(52) U.S. Cl. ...................................... 549/328; 549/329
(58) Field of Classification Search .................. 549/328, 549/329
See application file for complete search history.

(56) References Cited

U.S. PATENT DOCUMENTS

| 3,373,169 A | 3/1968 | Cherdron et al. |
| 5,998,635 A | 12/1999 | Miyano et al. |

FOREIGN PATENT DOCUMENTS

| EP | 0747336 | 12/1996 |
| JP | 47-25065 | 7/1972 |
| JP | 49-61153 | 6/1974 |
| JP | 5-004931 | 1/1993 |
| JP | 9-124521 | 5/1997 |

OTHER PUBLICATIONS

Record 1 of 1, Derwent Primary Accession No. 1974-70256V.*
Yang et al Journal of Organic Chemistry (1997), 62(1), 4-5.*
Article Titled "Studies of the Asymmetric [2+2] Cycloaddition of Silylketenes and Aldehydes Emplying Ti-TADDOL Catalysts" jointly authored by Yang et al., in Tetrahedron Letters, 39,1998, (pp. 2877-2880).
Article Titled "Cinchona Alkaloid-Lewis Acid Catalyst Systems for Enantioselective Ketene-Aldehyde Cycloadditions" jointly authored by Zhu et al., in J.Am.Chem.Soc., 126, Apr. 13, 2004, pp. 5352-5353.
Article Titled "Sequential Acyl Halide-Aldehyde Cyclocondensation and Enzymatic Resolution as a Route to Enantiomerically Enriched β-Lactones" jointly authored by Nelson et al., in J.Org.Chem, 65, 2000, (pp. 1227-1230).
Article Titled "Catalytic Asymmetric Acyl Halide-Aldehyde Cyclocondensations. A Strategy for Enantioselective Catalyzed Cross Aldol Reactions" jointly authored by Nelson, et al., in J.Am. Chem.Soc., 121, Apr. 10, 1999,(pp. 9742-9743).
Article Titled "Studies of the Tandem Mukaiyama Aldol-Lactonization (TMAL) Reaction: A Concise and Highly Diastereoselective Route to β-Lactones Applied to the Total Synthesis of the Potent Pancreatic Lipase Inhibitor, (-)-Panclicin D" jointly authored by Yang et al., in Tetrahedron, vol. 53, No. 48,1997,(pp. 16471-16488).
Article Titled "Synthesis and Intramolecular Ring Cleavage of 2-Oxetanones" jointly authored by Mead et al., in Tetrahedron Letters, vol. 29, No. 50,1988, (pp. 6573-6576).
Article Titled "Synthesis of Some Propiolactones with Aromatic Substituents in Position 3" jointly authored by FOMINA et al., in Chemical Abstracts, vol. 76, 1972, (p. 429).
Article Titled "Structural and Solvent Effects on the Mechanism of the Thermal Decarboxylation of 2-Oxetanones. A Limiting Case between Concerted and Stepwise Pathways in Pericyclic Reactions" jointly authored by Morao et al., in J.Am.Chem.Soc.,119,1997, (pp. 816-825).
Article Titled "Theoretical Study on the Mechanism of the Thermal Decarboxylation of 2-Oxetanones" jointly authored by Minato et al., in J.Org.Chem., 48, 1983, (pp. 1479-1483).
Article Titled "Studies in Spiroketal Synthesis 2. A Tandem Cyclization Route to the 1,7-Dioxaspiro[5.5]undecane Ring System" jointly authored by Mead et al., in Synlette, Nov. 1996,(pp. 1065-1066).
Hong Woon Yang et al., "Studies of the asymmetric [2+2] cycloaddition of silylketenes and aldehydes employing Ti-TADDOL catalysts" Tetrahedron Letters, vol. 39, No. 19, pp. 2877-2880, Dec. 31, 1998.
Keith T. Mead et al., "Synthesis and intramolecular ring cleavage of 2-oxetanones" Tetrahedron Letters, vol. 29, No. 50, pp. 6573-6576, Dec. 31, 1988.
Ana Arrieta et al., "Structural and solvent effects on the mechanism of the thermal decarboxylation of 2-oxetanones. A limiting case between concerted and stepwise pathways in pericyclic reactions" J. Am. Chem. Soc. vol. 119, No. 4, pp. 816-825, Dec. 31, 1997.

* cited by examiner

*Primary Examiner* — Nizal Chandrakumar
(74) *Attorney, Agent, or Firm* — J.C. Patents

(57) ABSTRACT

An aldehyde derivative represented by the general formula (2) is reacted with ketene in the presence of a Lewis acid catalyst to produce a novel 2-oxetanone derivative (1), which is then purified to a 2-oxetanone derivative having a high trans-isomer purity, and then converted to a vinyl derivative (3) through decarboxylation reaction.

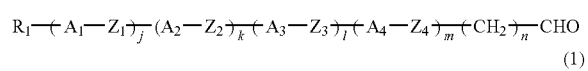

(2)

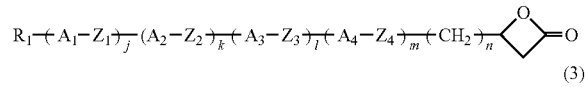

(1)

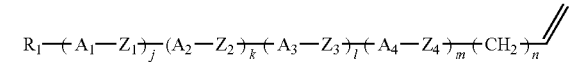

(3)

12 Claims, No Drawings

2-OXETANONE DERIVATIVE AND PROCESS FOR PRODUCTION THEREOF

TECHNICAL FIELD

The present invention relates to a novel 2-oxetanone derivative represented by the general formula (1) shown below. The 2-oxetanone derivative can be used as an intermediate for producing a vinyl derivative represented by the general formula (3) shown below. The invention relates to a 2-oxetanone derivative, a method for producing the 2-oxetanone derivative, and a method for producing a vinyl derivative. The vinyl derivative according to the invention, particularly a trans-isomer thereof, has good electric and optical characteristics and is useful as an intermediate material of a liquid crystal for display and as a liquid crystal.

BACKGROUND ART

As an ordinary method for producing a trans-4-ethenylcyclohexane derivative, a method using a Wittig reaction of a cyclohexanecarbaldehyde derivative and methyltriphenylphosphine halide has been known (see, for example, Patent Document 1).

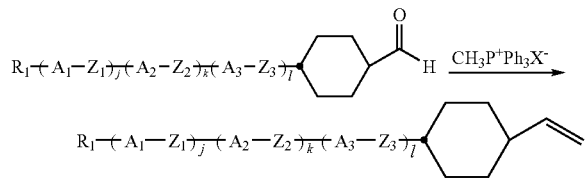

In this method, however, methyltriphenylphosphine halide as a raw material is expensive, and it is necessary to remove completely triphenylphosphine oxide by-produced for using the resulting trans-4-ethenylcyclohexane derivative as a liquid crystal raw material, which requires a complicated purification process. Furthermore, a disposal cost is required for discarding the triphenylphosphine oxide by-produced, and thus the method involves problems in cost and environment.

As a method for producing the cyclohexanecarbaldehyde derivative used as a raw material of the reaction, a method of subjecting a cyclohexanone compound represented by the general formula (6) to a Wittig reaction has been known.

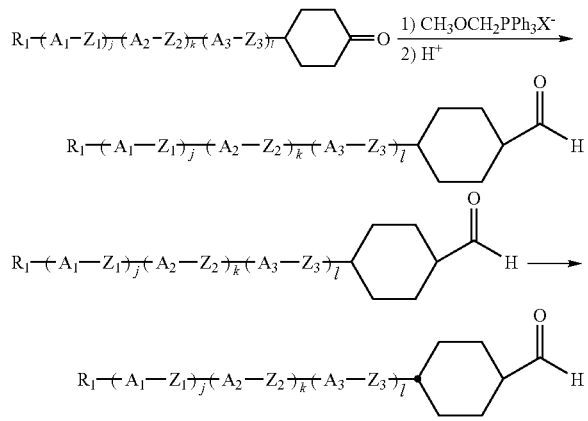

In the formula, $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N; $A_1$, $A_2$ and $A_3$ are each independently trans-1,4-cyclohexylene in which arbitrary —$CH_2$— constituting the ring may be replaced by —O— or —S—, 1,4-phenylene in which arbitrary hydrogen may be replaced by fluorine, decahydronaphthalen-2,6-diyl, 1,2,3,4-tetrahydronaphthalen-2,6-diyl or naphthalen-2,6-diyl; $Z_1$, $Z_2$ and $Z_3$ are each independently a single bond, —$CH_2CH_2$—, —$(CH_2)_4$—, —$CH_2O$— or —$OCH_2$—; and j, k and l are each independently 0 or 1.

As a method for producing the cyclohexanecarbaldehyde derivative, a method of oxidizing a carbinol compound represented by the general formula (7) has been known.

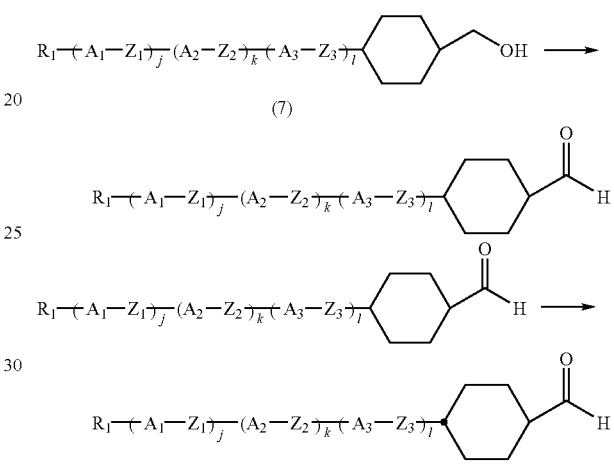

In the formula, $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N; $A_1$, $A_2$ and $A_3$ are each independently trans-1,4-cyclohexylene in which arbitrary —$CH_2$— constituting the ring may be replaced by —O— or —S—, 1,4-phenylene in which arbitrary hydrogen may be replaced by fluorine, decahydronaphthalen-2,6-diyl, 1,2,3,4-tetrahydronaphthalen-2,6-diyl or naphthalen-2,6-diyl; $Z_1$, $Z_2$ and $Z_3$ are each independently a single bond, —$CH_2CH_2$—, —$(CH_2)_4$—, —$CH_2O$— or —$OCH_2$—; and j, k and l are each independently 0 or 1.

However, a cyclohexanecarbaldehyde derivative obtained by these methods is a mixture of a trans-isomer and a cis-isomer since the hydrogen atom at the α-position of the carbonyl group of the aldehyde is easily epimerized (isomerized). A trans-4-ethenylcyclohexane derivative that has a high trans-isomer purity is necessarily used as a raw material of a liquid crystal for attaining good electric and optical characteristics. Accordingly, it is necessary to remove the cis-isomer from the resulting cyclohexanecarbaldehyde derivative, but the cis-isomer cannot be easily removed, and purification with recrystallization and column chromatography is necessarily performed (see, for example, Patent Document 2). Thus, the conventional methods are never satisfactory.

[Patent Document 1] JP H9-52851 A/1997 (U.S. Pat. No. 5,709,820)

[Patent Document 2] JP H9-124521 A/1997

DISCLOSURE OF THE INVENTION

Accordingly, an object of the invention is to provide a novel oxetanone derivative and a method for producing the same, and to provide a method for producing efficiently a vinyl derivative, for example, trans-4-ethenylcyclohexane derivative as a typical example thereof, by using the oxetanone derivative.

As a result of earnest investigations made by the inventors, a 2-oxetanone derivative represented by the general formula (1) has been found as an intermediate of a vinyl derivative, and it has also been found that a vinyl derivative represented by the general formula (3) can be produced efficiently by using the derivative, thereby the present invention has been completed.

Accordingly, the invention includes the followings.

[Item 1]

A 2-oxetanone derivative represented by the general formula (1):

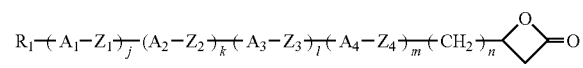
(1)

wherein $R_1$ is hydrogen, alkyl having 1 to 20 carbons, halogen, —C≡N, —C≡C—C≡N, —N=C=O or —N=C=S, wherein arbitrary —$CH_2$— may be replaced by —O—, —S—, —CO— or —$SiH_2$—, arbitrary —$(CH_2)_2$— may be replaced by —CH=CH— or —C≡C—, and arbitrary hydrogen may be replaced by halogen in the alkyl; $A_1$, $A_2$, $A_3$ and $A_4$ are each independently 1,4-cyclohexylene, 1,4-phenylene, decahydronaphthalen-2,6-diyl, 1,2,3,4-tetrahydronaphthalen-2,6-diyl or naphthalen-2,6-diyl, wherein arbitrary —$CH_2$— may be replaced by —O—, —S—, —CO— or —$SiH_2$—, arbitrary —$(CH_2)_2$— may be replaced by —CH=CH— and arbitrary hydrogen may be replaced by halogen in these rings, and arbitrary —CH= may be replaced by —N= in the 1,4-phenylene, provided that when $A_1$, $A_2$ and $A_3$ are each 1,4-cyclohexylene, the steric configuration thereof is trans, and when $A_4$ is 1,4-cyclohexylene, the steric configuration thereof may be trans, cis or a mixture of trans and cis; $Z_1$, $Z_2$, $Z_3$ and $Z_4$ are each independently a single bond, —$CH_2CH_2$—, —$(CH_2)_4$—, —$CH_2O$— or —$OCH_2$—; j, k and l are each independently 0 or 1; m is 1; and n is an integer of from 0 to 6.

[Item 2]

The 2-oxetanone derivative according to item 1 which is represented by the general formula (1-1):

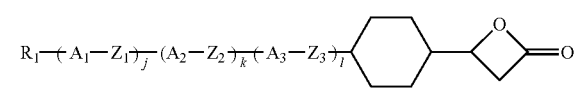
(1-1)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N; $A_1$, $A_2$ and $A_3$ are each independently trans-1,4-cyclohexylene in which arbitrary —$CH_2$— constituting the ring may be replaced by —O— or —S—, 1,4-phenylene in which arbitrary hydrogen may be replaced by fluorine, decahydronaphthalen-2,6-diyl, 1,2,3,4-tetrahydronaphthalen-2,6-diyl or naphthalen-2,6-diyl; $Z_1$, $Z_2$ and $Z_3$ are each independently a single bond, —$CH_2CH_2$—, —$(CH_2)_4$—, —$CH_2O$— or —$OCH_2$—; and j, k and l are each independently 0 or 1.

[Item 3]

A 2-oxetanone derivative represented by the general formula (1-2):

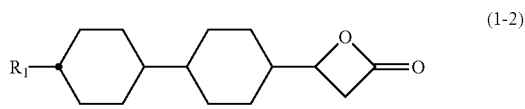
(1-2)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N.

[Item 4]

A 2-oxetanone derivative represented by the general formula (1-3):

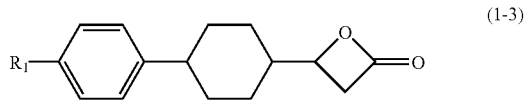
(1-3)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N.

[Item 5]

A 2-oxetanone derivative represented by the general formula (1-4):

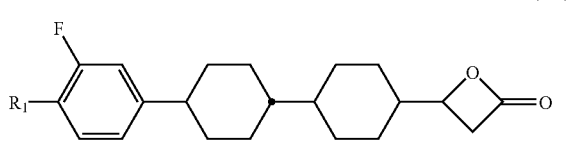
(1-4)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N.

[Item 6]

A 2-oxetanone derivative represented by the general formula (1-5):

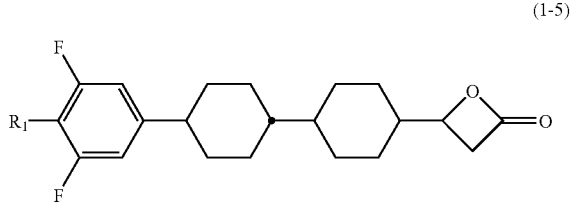
(1-5)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N.

[Item 7]

A 2-oxetanone derivative represented by the general formula (1-6):

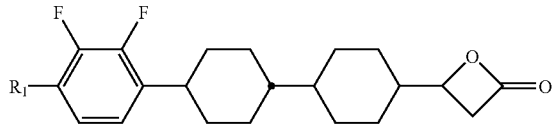
(1-6)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N.

[Item 8]

A 2-oxetanone derivative represented by the general formula (1-7):

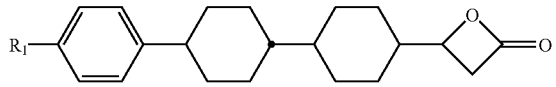
(1-7)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N.

[Item 9]

A 2-oxetanone derivative represented by the general formula (1-8):

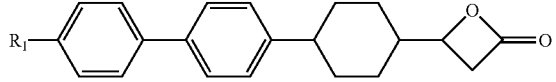
(1-8)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N.

[Item 10]

The 2-oxetanone derivative according to item 1 which is represented by the general formula (1-9):

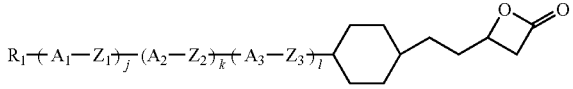
(1-9)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N; $A_1$, $A_2$ and $A_3$ are each independently trans-1,4-cyclohexylene in which arbitrary —$CH_2$— constituting the ring may be replaced by —O— or —S—, 1,4-phenylene in which arbitrary hydrogen may be replaced by fluorine, decahydronaphthalen-2,6-diyl, 1,2,3,4-tetrahydronaphthalen-2,6-diyl or naphthalen-2,6-diyl; $Z_1$, $Z_2$ and $Z_3$ are each independently a single bond, —$CH_2CH_2$—, —$(CH_2)_4$—, —$CH_2O$— or —$OCH_2$—; and j, k and l are each independently 0 or 1.

[Item 11]

A 2-oxetanone derivative represented by the general formula (1-10):

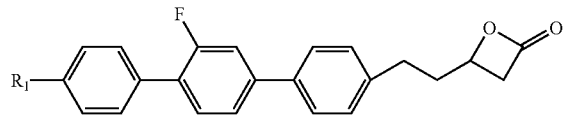
(1-10)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N.

[Item 12]

4-(4-(trans-4-propylcyclohexyl)cyclohexyl)-2-oxetanone, 4-(4-(trans-4-butylcyclohexyl)cyclohexyl)-2-oxetanone or 4-(4-(trans-4-pentylcyclohexyl)cyclohexyl)-2-oxetanone.

[Item 13]

A method for producing a 2-oxetanone derivative represented by the general formula (1), comprising reacting an aldehyde derivative represented by the general formula (2) with ketene in the presence of a Lewis acid catalyst:

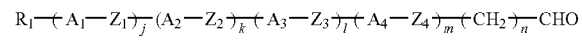
(2)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N; $A_1$, $A_2$, $A_3$ and $A_4$ are each independently 1,4-cyclohexylene in which arbitrary —$CH_2$— constituting the ring may be replaced by —O— or —S—, 1,4-phenylene in which arbitrary hydrogen may be replaced by fluorine, decahydronaphthalen-2,6-diyl, 1,2,3,4-tetrahydronaphthalen-2,6-diyl or naphthalen-2,6-diyl, provided that when $A_1$, $A_2$ and $A_3$ are each 1,4-cyclohexylene, the steric configuration thereof is trans, and when $A_4$ is 1,4-cyclohexylene, the steric configuration thereof may be trans, cis or a mixture of trans and cis; $Z_1$, $Z_2$, $Z_3$ and $Z_4$ are each independently a single bond, —$CH_2CH_2$—, —$(CH_2)_4$—, —$CH_2O$— or —$OCH_2$—; j, k and l are each independently 0 or 1; m is 1; and n is an integer of from 0 to 6,

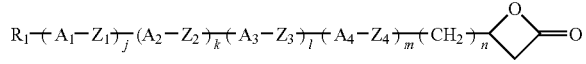
(1)

wherein $R_1$, $A_1$, $A_2$, $A_3$, $A_4$, $Z_1$, $Z_2$, $Z_3$, $Z_4$, j, k, l, m and n have the same meanings as in the formula (2).

[Item 14]

A method for producing a vinyl derivative represented by the general formula (3), comprising subjecting a 2-oxetanone derivative represented by the general formula (1) to decarboxylation under heating:

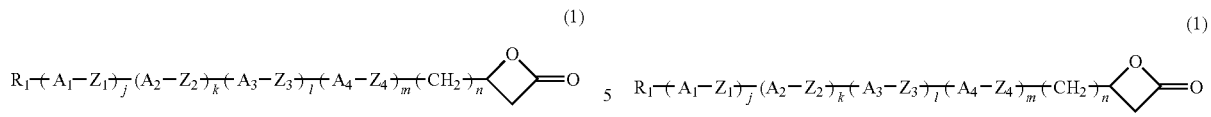
(1)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N; $A_1, A_2, A_3$ and $A_4$ are each independently 1,4-cyclohexylene in which arbitrary —$CH_2$— constituting the ring may be replaced by —O— or —S—, 1,4-phenylene in which arbitrary hydrogen may be replaced by fluorine, decahydronaphthalen-2,6-diyl, 1,2,3,4-tetrahydronaphthalen-2,6-diyl or naphthalen-2,6-diyl, provided that when $A_1$, $A_2$ and $A_3$ are each 1,4-cyclohexylene, the steric configuration thereof is trans, and when $A_4$ is 1,4-cyclohexylene, the steric configuration thereof may be trans, cis or a mixture of trans and cis; $Z_1, Z_2, Z_3$ and $Z_4$ are each independently a single bond, —$CH_2CH_2$—, —$(CH_2)_4$—, —$CH_2O$— or —$OCH_2$—; j, k and l are each independently 0 or 1; m is 1; and n is an integer of from 0 to 6,

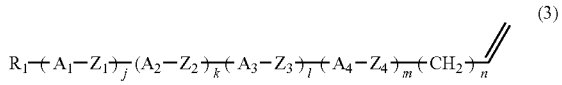
(3)

wherein $R_1, A_1, A_2, A_3, A_4, Z_1, Z_2, Z_3, Z_4$, j, k, l, m and n have the same meanings as in the formula (1).

[Item 15]

A method for producing a vinyl derivative represented by the general formula (3), comprising reacting an aldehyde derivative represented by the general formula (2) with ketene in the presence of a Lewis acid catalyst to produce a 2-oxetanone derivative represented by the general formula (1); purifying the compound represented by the general formula (1) wherein $A_4$ is trans-1,4-cyclohexylene in which arbitrary —$CH_2$— constituting the ring may be replaced by —O— or —S—, through recrystallization; and subjecting the compound to decarboxylation under heating:

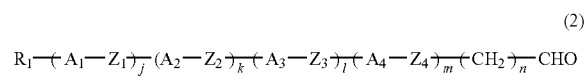
(2)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N; $A_1, A_2$ and $A_3$ are each independently trans-1,4-cyclohexylene in which arbitrary —$CH_2$— constituting the ring may be replaced by —O— or —S—, 1,4-phenylene in which arbitrary hydrogen may be replaced by fluorine, decahydronaphthalen-2,6-diyl, 1,2,3,4-tetrahydronaphthalen-2,6-diyl or naphthalen-2,6-diyl; $A_4$ is 1,4-cyclohexylene in which arbitrary —$CH_2$— constituting the ring may be replaced by —O— or —S—; $Z_1, Z_2, Z_3$ and $Z_4$ are each independently a single bond, —$CH_2CH_2$—, —$(CH_2)_4$—, —$CH_2O$— or —$OCH_2$—; j, k and l are each independently 0 or 1; m is 1; and n is an integer of from 0 to 6,

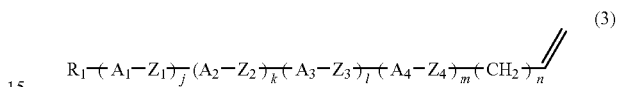
(1)

wherein $R_1, A_1, A_2, A_3, A_4, Z_1, Z_2, Z_3, Z_4$, j, k, l, m and n have the same meanings as in the formula (2),

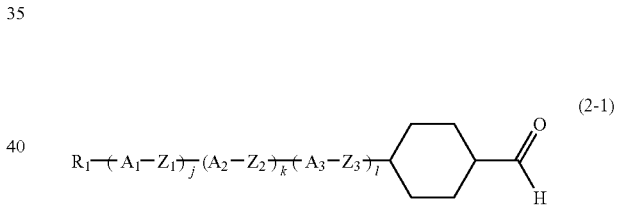
(3)

wherein $R_1, A_1, A_2, A_3, A_4, Z_1, Z_2, Z_3, Z_4$, j, k, l, m and n have the same meanings as in the formula (2), provided that $A_4$ is trans-1,4-cyclohexylene in which arbitrary —$CH_2$— constituting the ring may be replaced by —O— or —S—.

[Item 16]

A method for producing a vinyl derivative represented by the general formula (3-1) wherein 1,4-cyclohexylene bonded to aldehyde has a trans-isomer, comprising reacting an aldehyde derivative represented by the general formula (2-1) with ketene in the presence of a Lewis acid catalyst to produce a 2-oxetanone derivative represented by the general formula (1-1); purifying the compound represented by the general formula (1-1) wherein 1,4-cyclohexylene bonded to aldehyde has a trans-isomer through recrystallization; and subjecting the compound to decarboxylation under heating:

(2-1)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N; $A_1, A_2$ and $A_3$ are each independently trans-1,4-cyclohexylene in which arbitrary —$CH_2$— constituting the ring may be replaced by —O— or —S—, 1,4-phenylene in which arbitrary hydrogen may be replaced by fluorine, decahydronaphthalen-2,6-diyl, 1,2,3,4-tetrahydronaphthalen-2,6-diyl or naphthalen-2,6-diyl; $Z_1, Z_2$ and $Z_3$ are each independently a single bond, —$CH_2CH_2$—, —$(CH_2)_4$—, —$CH_2O$— or —$OCH_2$—; and j, k and l are each independently 0 or 1,

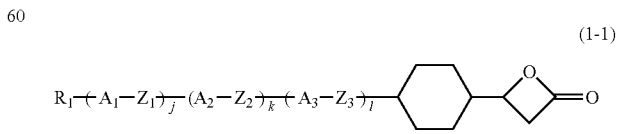
(1-1)

wherein $R_1$, $A_1$, $A_2$, $A_3$, $Z_1$, $Z_2$, $Z_3$, j, k and l have the same meanings as in the formula (2-1),

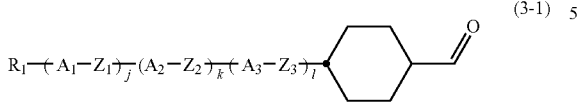
(3-1)

wherein $R_1$, $A_1$, $A_2$, $A_3$, $Z_1$, $Z_2$, $Z_3$, j, k and l have the same meanings as in the formula (2-1).

According to the invention, a novel 2-oxetanone derivative as a synthesis intermediate of a liquid crystal material can be provided from an aldehyde derivative. A vinyl derivative having a high purity and containing no triphenylphosphine oxide can be synthesized through decarboxylation reaction of the 2-oxetanone derivative. From the 2-oxetanone derivative of the invention, the cis-isomer can be easily removed through recrystallization to provide a 2-oxetanone derivative having high trans-isomer purity.

BEST MODE FOR CARRYING OUT THE INVENTION

The 2-oxetanone derivative of the invention is represented by formula (1):

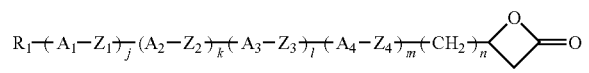
(1)

In the formula, $R_1$ is hydrogen, alkyl having 1 to 20 carbons, halogen, —C≡N, —C≡C—C≡N, —N=C=O or —N=C=S, wherein arbitrary —CH$_2$— may be replaced by —O—, —S—, —CO— or —SiH$_2$—, arbitrary —(CH$_2$)$_2$— may be replaced by —CH=CH— or —C≡C—, and arbitrary hydrogen may be replaced by halogen in the alkyl; $A_1$, $A_2$, $A_3$ and $A_4$ are each independently 1,4-cyclohexylene, 1,4-phenylene, decahydronaphthalen-2,6-diyl, 1,2,3,4-tetrahydronaphthalen-2,6-diyl or naphthalen-2,6-diyl, wherein arbitrary —CH$_2$— may be replaced by —O—, —S—, —CO— or —SiH$_2$—, arbitrary —(CH$_2$)$_2$— may be replaced by —CH=CH— and arbitrary hydrogen may be replaced by halogen in these rings, and arbitrary —CH= may be replaced by —N= in the 1,4-phenylene, provided that when $A_1$, $A_2$ and $A_3$ are each 1,4-cyclohexylene, the steric configuration thereof is trans, and when $A_4$ is 1,4-cyclohexylene, the steric configuration thereof may be trans, cis or a mixture of trans and cis; $Z_1$, $Z_2$, $Z_3$ and $Z_4$ are each independently a single bond, —CH$_2$CH$_2$—, —(CH$_2$)$_4$—, —CH$_2$O— or —OCH$_2$—; j, k and l are each independently 0 or 1; m is 1; and n is an integer of from 0 to 6.

The 2-oxetanone derivative represented by the general formula (1) includes the following compounds, but is not limited to the following compounds.

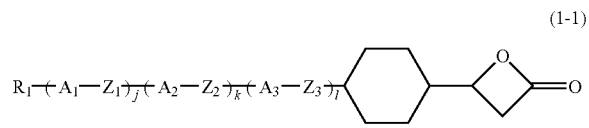
(1-1)

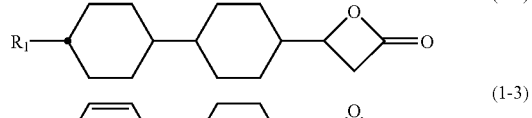
(1-2)
(1-3)

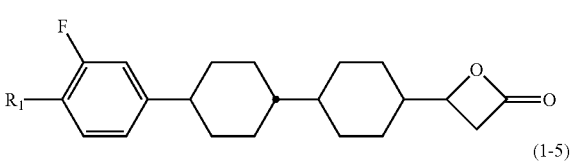
(1-4)
(1-5)

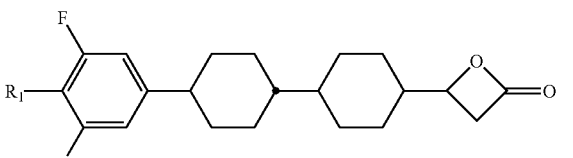
(1-6)
(1-7)

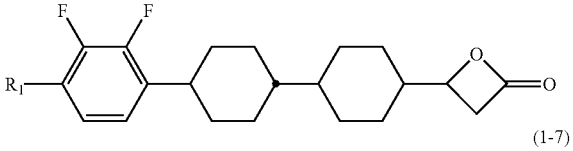
(1-8)
(1-9)

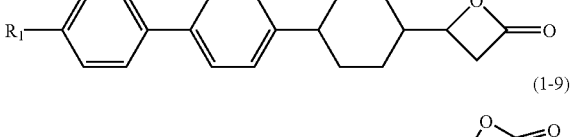
(1-10)

In the formulas (1-1) to (1-10), $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N.

In the formulas (1-1) to (1-9), $A_1$, $A_2$ and $A_3$ are each independently trans-1,4-cyclohexylene in which arbitrary —CH$_2$— constituting the ring may be replaced by —O— or —S—, 1,4-phenylene in which arbitrary hydrogen may be replaced by fluorine, decahydronaphthalen-2,6-diyl, 1,2,3,4-tetrahydronaphthalen-2,6-diyl or naphthalen-2,6-diyl; $Z_1$, $Z_2$ and $Z_3$ are each independently a single bond, —CH$_2$CH$_2$—, —(CH$_2$)$_4$—, —CH$_2$O— or —OCH$_2$—; and j, k and l are each independently 0 or 1.

Examples of (1-2) include 4-(4-(trans-4-propylcyclohexyl)cyclohexyl)-2-oxetanone, 4-(4-(trans-4-butylcyclohexyl)cyclohexyl)-2-oxetanone, 4-(4-(trans-4-pentylcyclohexyl)cyclohexyl)-2-oxetanone and the like.

Examples of (1-7) include 4-(4-(trans-4-(4-methylphenyl)cyclohexyl)cyclohexyl)-2-oxetanone and the like.

The method for producing the oxetanone derivative will be described.

The 2-oxetanone derivative (1) can be produced by introducing ketene to an organic solvent solution of an aldehyde derivative (2) and a catalytic amount of a Lewis acid. An aldehyde derivative to be used herein is represented by the general formula (2):

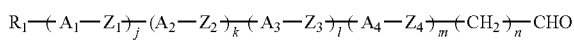

(2)

wherein $R_1$, $A_1$, $A_2$, $A_3$, $A_4$, $Z_1$, $Z_2$, $Z_3$, $Z_4$, j, k, l, m and n have the same meanings as in the formula (1). The compound represented by the general formula (2) can be synthesized by a method that has been reported. The compound represented by the general formula (2) can be synthesized by a method that is disclosed in the known literatures. Representative examples of the literatures for synthesis are shown below. 4-(trans-4-Propylcyclohexyl)cyclohexylcarbaldehyde: JP H9-124521 A/1997 and Liquid Crystal, 10, 261 (1991), 4-(trans-4-pentylcyclohexyl)cyclohexylcarbaldehyde: U.S. Pat. No. 4,323,473, 4-(4-cycnophenyl)cyclohexylcarbaldehyde, 4-(trans-4-(3,4-difluorophenyl)cyclohexyl)cyclohexyl-carbaldehyde: U.S. Pat. No. 5,185,098, 4-(trans-4-(3,4,5-trifluorophenyl)cyclohexyl)cyclohexyl-carbaldehyde: JP H6-211711 A/1994, 4-(trans-4-(3-fluoro-4-methylphenyl)cyclohexyl)cyclohexyl-carbaldehyde: Liquid Crystal, 16, 491 (1994), 4-(trans-4-(4-methylphenyl)cyclohexyl)cyclohexyl-carbaldehyde: Liquid Crystal, 16, 491 (1991), 3-(trans-4-(4-cyanophenyl)cyclohexyl)propanal: JP H1-216967 A/1989, 3-(trans-4-(trans-4-propylcyclohexyl)cyclohexyl)propanal: JP H1-175947 A/1989, [1,1':4',1"-terphenyl]-4-propanal: Journal of American Chemical Society, 126, 2807 (2004)

The ketene to be used for reaction with the aldehyde derivative represented by the general formula (2) may be one obtained by an ordinary production method, and for example, ketene obtained by thermal decomposition of acetone, thermal decomposition of acetic acid, and the like may be used.

As the Lewis acid, various kinds of Lewis acids may be used, such as aluminum chloride, aluminum bromide, zinc chloride, iron chloride, zinc bromide, titanium chloride, boron chloride, boron bromide and the like, and in particular, iron chloride and a boron trifluoride ether complex are preferred from the standpoint of activity. The catalyst is generally used in a range of from 0.01 to 20% by mol, and preferably in a range of from 0.1 to 10% by mol, based on the aldehyde derivative.

As the organic solvent, a solvent capable of dissolving the aldehyde derivative may be used. Examples thereof include a haloalkane, such as dichloromethane, chloroform and the like, an ester, such as ethyl acetate and the like, an alkylbenzene, such as toluene and the like, an ether solvent, such as diethyl ether, tetrahydrofuran and the like, and mixed solvents thereof. The using amount of the organic solvent is not particularly limited, and the organic solvent is generally used in a range of about from 0.5 to 30 times the aldehyde derivative (2) by weight.

The reaction with ketene is performed in the solvent, and the order of charging the ketene and the aldehyde derivative (2) is not particularly limited, and whichever may be charged firstly. The reaction temperature may be in a range of from −78 to 100° C., and preferably in a range of from −40 to 30° C.

The resulting 2-oxetanone derivative may be purified by such a method as recrystallization or the like.

The recrystallization may be performed on standing still or on stirring. Crystals thus deposited may be separated by a known method, such as filtration, suction filtration, centrifugal separation and the like. In the case where the crystals deposited contain the cis-isomer (i.e., the compound represented by the general formula (1) where the steric configuration of $A_4$ is cis), the resulting crystals may be further recrystallized to lower the content of the cis-isomer. The mother liquid recovered may be again subjected to recrystallization to recover the trans-isomer (i.e., the compound represented by the general formula (1) where the steric configuration of $A_4$ is trans) with high purity. Repetitive operation of recrystallization enables effective recovery and purification of the trans-isomer from the mother liquid.

Specifically, the 2-oxetanone derivative represented by the general formula (1) is dissolved in a suitable organic solvent to prepare a saturated solution. The saturated solution can be formed by dissolving the 2-oxetanone derivative represented by the general formula (1) under heating, or by concentrating the solution. Preferred examples of the solvent include a hydrocarbon solvent, such as hexane, heptane, cyclohexane, toluene and the like, an ether solvent, such as diethyl ether, dibutyl ether and the like, an ester solvent, such as methyl acetate, ethyl acetate, propyl acetate and the like, an alcohol solvent, such as methanol, ethanol, isopropanol and the like, and mixed solvents thereof.

The concentration of the 2-oxetanone derivative in the saturated solution varies depending on the solvent used and the crystallization temperature, and in general, is preferably in a range of from 3 to 40% by weight.

The vinyl derivative represented by the general formula (3) can be produced by subjecting the 2-oxetanone derivative (trans-isomer) represented by the general formula (1) to decarboxylation. The decarboxylation reaction in the present invention is generally performed in a range of from 100 to 250° C., and preferably in a range of from 150 to 200° C. The temperature is preferably 100° C. or more for providing a sufficient reaction rate, and is preferably 250° C. or less for preventing polymerization, decomposition and isomerization of the vinyl group from occurring.

A solvent and a catalyst are not always necessary, but may be used for controlling the reaction temperature. Examples of the solvent to be used include an ester solvent, such as hexyl acetate, octyl acetate, butyl acetate and the like, a non-protonic polar solvent, such as dimethylsulfoxide, dimethylamide and the like, and the like. The using amount of the organic solvent is not particularly limited, and is generally from 0.5 to 30 times the 2-oxetanone derivative by weight.

It is sometimes preferable that an antioxidant is added before starting the decarboxylation reaction for enhancing the storage stability of the coarse liquid of the vinyl derivative obtained through the decarboxylation reaction. Examples of the antioxidant include BTH. The addition amount of the antioxidant is from 1 to 10,000 ppm, and particularly preferably from 10 to 500 ppm, based on the 2-oxetanone derivative.

The trans-isomer of the 2-oxetanone derivative with high purity is obtained through recrystallization in the aforementioned manners, and then the trans-isomer of the vinyl derivative (i.e., the compound represented by the general formula (3) where the steric configuration of $A_4$ is trans) with high purity can be produced by subjecting the 2-oxetanone derivative to decarboxylation. The trans-isomer of the vinyl derivative is particularly useful as a material for liquid crystal and the like.

EXAMPLES $^1$H-NMR: A proton nuclear magnetic resonance spectrum was measured with GSX400 (400 MHz) of JEOL Ltd. with tetramethylsilane as an internal standard. Analysis of cis- and trans-isomers of the 4-substituted cyclohexyl-2-oxetanone derivative was calculated from the methine proton ratio of the β-lactone ring in $^1$H-NMR. The advantages of the present invention will be described with reference to examples below, but the present invention is not limited thereto.

Example 1

Synthesis of 4-(4-(trans-4-propylcyclohexyl)-cyclohexyl)-2-oxetanone 4-(trans-4-Propylcyclohexyl)cyclohexylcarbaldehyde (1 g, 3.8 mmol, ratio of trans-4-(trans-4-propylcyclohexane)-cyclohexanecarbaldehyde/cis-4-(trans-4-propylcyclohexyl)-cyclohexanecarbaldehyde=99.7/0.3) was dissolved in ethyl acetate (9 g), and iron chloride (FeCl$_3$, 10 mg, 0.06 mmol) was added thereto. 1.3 equivalents of ketene was introduced into the solution at 30° C. over 60 minutes. After completing the introduction of ketene, nitrogen was introduced for 30 minutes to eliminate the unreacted ketene, and the reaction was terminated by adding an aqueous solution having dissolved therein NaHCO$_3$ (31 mg, 0.37 mmol) corresponding to 6 equivalents of the catalyst. The resulting solution was concentrated to provide 4-(4-(trans-4-propylcyclohexyl)cyclohexyl)-2-oxetanone (ratio of 4-(trans-4-(trans-4-propylcyclohexyl)cyclohexyl)-2-oxetanone/4-(cis-4-(trans-4-propylcyclohexyl)cyclohexyl)-2-oxetanone=99.7/0.3) (0.90 g, 2.8 mmol, yield: 74%)).

The $^1$H-NMR spectrum was substantially the same as 4-(trans-4-(trans-4-propylcyclohexyl)cyclohexyl)-2-oxetanone shown in Example 2, but the methine group of 2-oxetanone having cyclohexyl substituted thereon derived from 4-(cis-4-(trans-4-propylcyclohexyl)cyclohexyl)-2-oxetanone was observed in the following region.

$^1$H-NMR (CDCl$_3$)δ: 4.46-4.51 (m, cyclohexyl-CH)

Example 2

Purification of 4-(trans-4-(trans-4-propyl-cyclohexyl)cyclohexyl)-2-oxetanone

The mixture of 4-(trans-4-(trans-4-propylcyclohexyl)-cyclohexyl)-2-oxetanone/4-(cis-4-(trans-4-propyl-cyclohexyl)cyclohexyl)-2-oxetanone=99.7/0.3 synthesized in Example 1 was coarsely purified with silica gel chromatography, and then dissolved in ethyl acetate (4 mL) at 30° C., followed by cooling to 5° C. Crystals deposited after lapsing 5 minutes were suction-filtered and dried under reduced pressure to provide 4-(trans-4-(trans-4-propylcyclohexyl)cyclohexyl)-2-oxetanone/4-(cis-4-(trans-4-propylcyclohexyl)cyclohexyl)-2-oxetanone=100/0 (0.90 g, 2.8 mmol, yield: 74%).

$^1$H-NMR (CDCl$_3$)δ: 0.82-1.81 (m, 26H, CH$_3$, CH$_3$—CH$_2$—CH$_2$, CH$_2$—CH$_2$—CH, (CH$_2$)$_3$—CH, CH—CH$_2$—CH$_2$×8, CH—CH—(CH$_2$)$_2$×2), 1.99-2.01 (m, 1H, —CH-4-oxetanone), 3.11, 3.42 (dd, 2H, J=16.14.4 Hz, J=16.1 5.9 Hz, CH—CH$_2$—CO), 4.15-4.20 (m, 1H, cyclohexyl-CH)

Example 3

Synthesis of trans-1-ethenyl-4-(trans-4-propyl-cyclohexyl)cyclohexane 4-(trans-4-(trans-4-Propylcyclohexyl)cyclohexyl)-2-oxetanone (1 g, 3.1 mmol) obtained in Example 2 was placed in a reactor, the interior of which was then sufficiently replaced by nitrogen. The reactor was heated, and after heating to 170° C. for 3 hours, it was cooled to room temperature. The resulting solid was dissolved in heptane and purified with silica gel chromatography to provide trans-1-ethenyl-4-(trans-4-propyl-cyclohexyl)cyclohexane (0.83 g, 30 mmol, yield: 95%).

Example 4

Synthesis of 4-(4-(trans-4-pentylcyclohexyl)-cyclohexyl)-2-oxetanone

In the same manner as in Example 1, 4-(4-(trans-4-pentylcyclohexyl)cyclohexyl)-2-oxetanone (ratio of 4-(trans-4-(trans-4-pentylcyclohexyl)cyclohexyl)-2-oxetanone/4-(cis-4-(trans-4-pentylcyclohexyl)cyclohexyl)-2-oxetanone=98/2 (yield: 70%)) was obtained by using 4-(trans-4-pentylcyclohexyl)cyclohexylcarbaldehyde (1 g, 3.8 mmol, ratio of trans-4-(trans-4-pentylcyclohexyl)cyclohexyl-carbaldehyde/cis-4-(trans-4-pentylcyclohexyl)cyclohexyl-carbaldehyde=98/2).

The $^1$H-NMR spectrum was substantially the same as 4-(trans-4-(trans-4-pentylcyclohexyl)cyclohexyl)-2-oxetanone shown in Example 5, but the methine group of 2-oxetanone having cyclohexyl substituted thereon derived from 4-(cis-4-(trans-4-pentylcyclohexyl)cyclohexyl)-2-oxetanone was observed in the following region.

$^1$H-NMR (CDCl$_3$)δ: 4.46-4.51 (m, cyclohexyl-CH)

Example 5

Purification of 4-(trans-4-(trans-4-pentyl-cyclohexyl)cyclohexyl)-2-oxetanone

Ethyl acetate (40 mL) was added to the mixture of 4-(trans-4-(trans-4-pentylcyclohexyl)cyclohexyl)-2-oxetanone and 4-(cis-4-(trans-4-pentylcyclohexyl)cyclohexyl)-2-oxetanone (mixing ratio: 98/2, 10.8 g, 28.1 mmol) synthesized in Example 4 and coarsely purified with silica gel chromatography, to dissolve the mixture at 30° C., followed by cooling to −20° C. Crystals deposited after lapsing 5 minutes were suction-filtered and dried under reduced pressure to provide 4-(trans-4-(trans-4-pentylcyclohexyl)cyclohexyl)-2-oxetanone/4-(cis-4-(trans-4-pentylcyclohexyl)cyclohexyl)-2-oxetanone=99.9/0.1 (8.3 g, 25.8 mmol, yield: 92%). Ethyl acetate (30 mL) was added to the resulting crystals, and the same operation was performed to provide 4-(trans-4-(trans-4-pentylcyclohexyl)cyclohexyl)-2-oxetanone (trans-isomer: 100%, 7.3 g, 24.2 mmol, yield: 94%).

$^1$H-NMR (CDCl$_3$)δ: 0.82-1.81 (m, 30H, CH$_3$, CH$_3$—CH$_2$—CH$_2$, CH$_2$—CH$_2$—CH$_2$×2, CH$_2$—CH$_2$—CH, (CH$_2$)$_3$—CH, CH—CH$_2$—CH$_2$×8, CH—CH—(CH$_2$)$_2$×2), 1.99-2.01 (m, 1H, (CH$_2$)CH-4-oxetanone), 3.11, 3.42 (dd, 2H, J=16.14.4 Hz, J=16.15.9 Hz, CH—CH$_2$—CO), 4.15-4.20 (m, 1H, cyclohexyl-CH)

Example 6

Synthesis of trans-1-ethenyl-4-(trans-4-pentyl-cyclohexyl)cyclohexane 4-(trans-4-(trans-4-pentylcyclohexyl)cyclohexyl)-2-oxetanone obtained in Example 5 was placed in a reactor, the interior of which was then sufficiently replaced by nitrogen. The reactor was heated, and after heating to 170° C. for 3 hours, it was cooled to room temperature. The resulting solid was dissolved in heptane and purified with silica gel chromatography to provide trans-1-ethenyl-4-(trans-4-pentylcyclohexyl)-cyclohexane at a yield of 95%.

Example 7

Synthesis of 4-(4-(trans-4-(4-methylphenyl)-cyclohexyl)cyclohexyl)-2-oxetanone 4-(trans-4-(4-methylphenyl)cyclohexyl)cyclohexane-carbaldehyde (20.6 g, 72 mmol, ratio of trans-4-(trans-4-(4-methylphenyl)cyclohexyl)cyclohexanecarbaldehyde/cis-4-(trans-4-(4-methylphenyl)cyclohexyl)-cyclohexylcarbaldehyde=98/2) was dissolved in ethyl acetate (380 g), and iron chloride (FeCl$_3$, 0.2 g, 1.2 mmol) was added thereto. 3.7 equivalents of ketene was introduced into the solution at 40° C. over 150 minutes. After completing the introduction of ketene, nitrogen was introduced for 30 minutes to eliminate the unreacted ketene. The resulting solution was concentrated to provide 4-(4-(trans-4-(4-methylphenyl)-cyclohexyl)cyclohexyl)-2-oxetanone (ratio of 4-(trans-4-(trans-4-(4-methylphenyl)cyclohexyl)cyclohexyl)-2-oxetanone/4-(cis-4-(trans-4-(4-methylphenyl)cyclohexyl)-cyclohexyl)-2-oxetanone=98/2) (27.8 g, 64 mmol, yield: 88%)).

The $^1$H-NMR spectrum was substantially the same as 4-(trans-4-(trans-4-(4-methylphenyl)cyclohexyl)cyclohexyl)-2-oxetanone shown in Example 8, but the methine group of 2-oxetanone having cyclohexyl substituted thereon derived from 4-(cis-4-(trans-4-(4-methylphenyl)cyclohexyl)cyclohexyl)-2-oxetanone was observed in the following region.

$^1$H-NMR (CDCl$_3$)δ: 4.48-4.51 (m, cyclohexyl-C$\underline{H}$—O)

Example 8

Purification of 4-(trans-4-(trans-4-(4-methyl-phenyl)cyclohexyl)cyclohexyl)-2-oxetanone The mixture of 4-(trans-4-(trans-4-(4-methylphenyl)-cyclohexyl)cyclohexyl)-2-oxetanone and 4-(cis-4-(trans-4-(4-methylphenyl)cyclohexyl)cyclohexyl)-2-oxetanone=98/2 synthesized in Example 7 was coarsely purified with silica gel chromatography, and then dissolved in toluene (80 mL) at 60° C., and then heptane (20 mL) was added thereto, followed by cooling to −40° C. Crystals deposited after lapsing 5 minutes were suction-filtered and dried under reduced pressure to provide 4-(trans-4-(trans-4-(4-methylphenyl)cyclohexyl)cyclohexyl)-2-ox etanone/4-(cis-4-(trans-4-(4-methylphenyl)cyclohexyl)-cyclohexyl)-2-oxetanone=99.8/0.2 (17.0 g, 52 mmol, yield: 94%). The resulting crystals were subjected to the same operation by using toluene (68 mL) and heptane (17 mL) to provide 4-(trans-4-(trans-4-(4-methylphenyl)cyclohexyl)cyclohexyl)-2-oxetanone (trans-isomer: 100%, 16.2 g, 50 mmol, yield: 97%).

$^1$H-NMR (CDCl$_3$)δ: 1.04-1.92 (m, 18H, CH—C$\underline{H}_2$—C$\underline{H}_2$×8, C$\underline{H}$—CH—(CH$_2$)$_2$×2), 2.02-2.05 (m, 1H, —C$\underline{H}$-4-oxetanone), 2.31 (s, 3H, Ph-CH$_3$), 2.38-2.45 (m, 1H, Ph-C$\underline{H}$—(CH$_2$)$_2$, 3.10, 3.42 (dd, 2$\underline{H}$, J=16.1 Hz 4.4 Hz, J=16.$\overline{5}$5.9 Hz, CH—C$\underline{H}_2$—CO), 4.17-4.19 (m, 1H, cyclohexyl-C$\underline{H}$—O), 7.10 (s, $\overline{4}$H, Ph-$\underline{H}$)

Example 9

Synthesis of trans-1-ethenyl-4-(trans-4-(4-methylphenyl)cyclohexyl)cyclohexane 4-(trans-4-(trans-4-(4-Methylphenyl)cyclohexyl)-cyclohexyl)-2-oxetanone (3 g, 9.2 mmol) obtained in Example 8 was placed in a reactor, the interior of which was then sufficiently replaced by nitrogen. The reactor was heated, and after heating to 170° C. for 3 hours, it was cooled to room temperature. The resulting solid was dissolved in heptane and purified with silica gel chromatography to provide trans-1-ethenyl-4-(trans-4-(4-methylphenyl)cyclohexyl)-cyclohexane (2.4 g, 8.5 mmol, yield: 89%).

The 2-oxetanone derivatives (compound (1) to compound (98)) shown below can be easily produced according to the method disclosed in Examples.

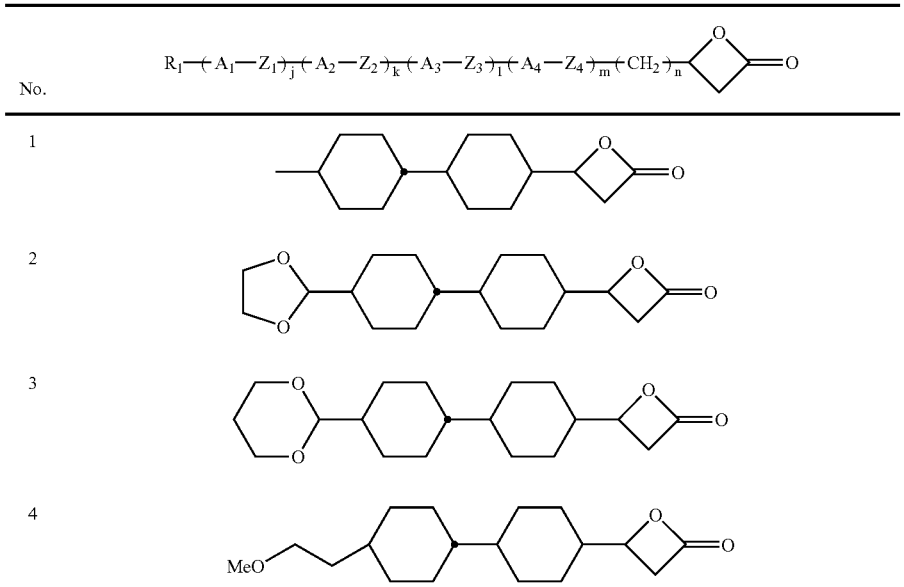

-continued
| No. | $R_1-(A_1-Z_1)_j-(A_2-Z_2)_k-(A_3-Z_3)_l-(A_4-Z_4)_m-(CH_2)_n-\underset{O}{\overset{O}{\square}}=O$ |
|---|---|
| 5 | 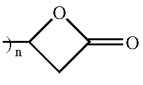 |
| 6 | 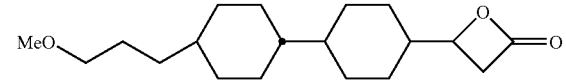 |
| 7 | 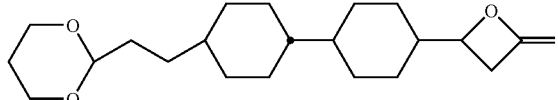 |
| 8 | 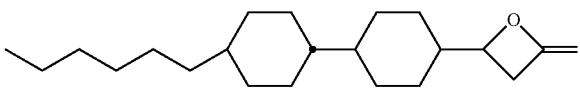 |
| 9 | 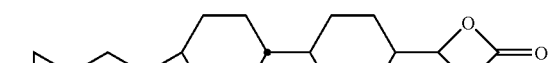 |
| 10 |  |
| 11 | 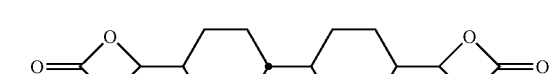 |
| 12 | 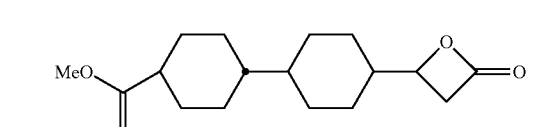 |
| 13 | 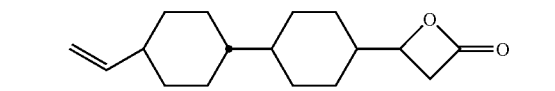 |
| 14 | 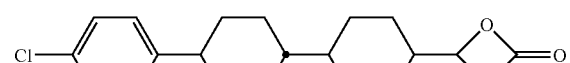 |
| 15 | 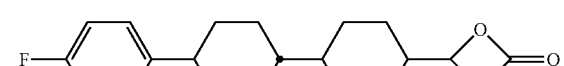 |
| 16 | 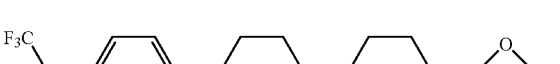 |
| 17 | 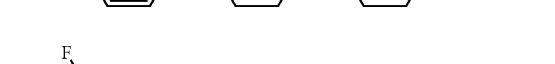 |

-continued
| No. | $R_1-(A_1-Z_1)_j-(A_2-Z_2)_k-(A_3-Z_3)_l-(A_4-Z_4)_m-(CH_2)_n-\text{(oxetanone)}$ |
|---|---|
| 18 | 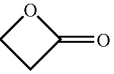 |
| 19 | 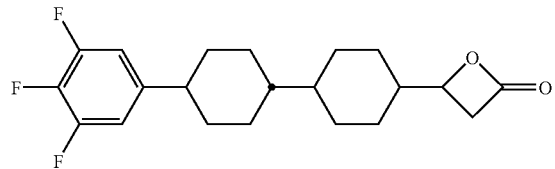 |
| 20 | 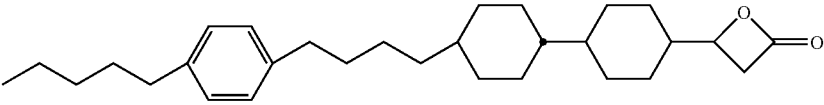 |
| 21 | 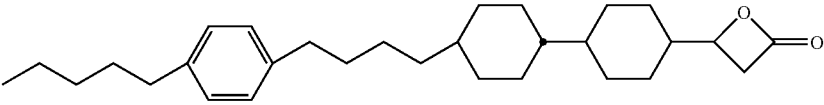 |
| 22 | 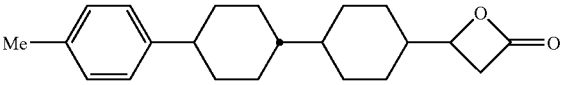 |
| 23 | 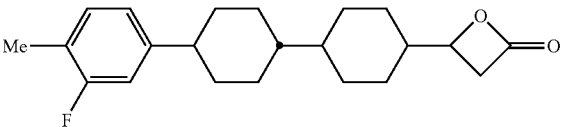 |
| 24 | 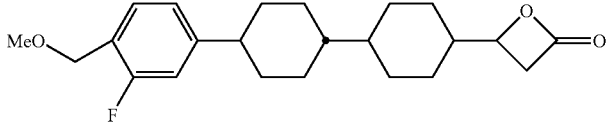 |
| 25 | 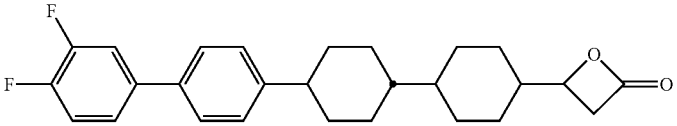 |
| 26 | 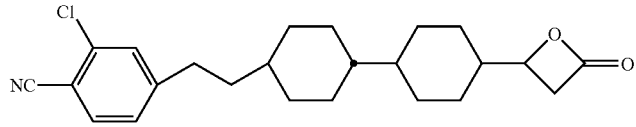 |
| 27 | 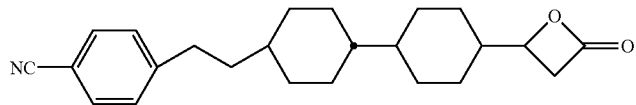 |
| 28 | 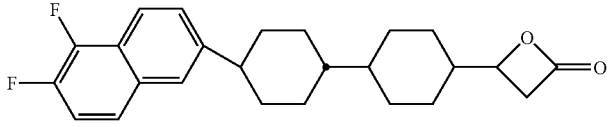 |

-continued

| No. | $R_1-(A_1-Z_1)_j-(A_2-Z_2)_k-(A_3-Z_3)_l-(A_4-Z_4)_m-(CH_2)_n-\text{(oxetanone)}$ |
|---|---|
| 29 | 3,4-difluorophenyl-cyclohexyl-β-lactone |
| 30 | 4-cyano-3-fluorophenyl-cyclohexyl-β-lactone |
| 31 | 3,4,5-trifluorophenyl-cyclohexyl-β-lactone |
| 32 | 4-bromophenyl-cyclohexyl-β-lactone |
| 33 | 4-ethoxy-2,3-difluorophenyl-cyclohexyl-β-lactone |
| 34 | 4-cyano-3,5-difluorophenyl-cyclohexyl-β-lactone |
| 35 | 4-fluorophenyl-cyclohexyl-β-lactone |
| 36 | 4-chlorophenyl-cyclohexyl-β-lactone |
| 37 | 4-propylphenyl-ethyl-phenyl-cyclohexyl-β-lactone |
| 38 | 2,3-difluorophenyl-cyclohexyl-β-lactone |
| 39 | 4-trifluoromethoxy-3-fluorophenyl-cyclohexyl-β-lactone |

-continued

| No. | $R_1-(A_1-Z_1)_j-(A_2-Z_2)_k-(A_3-Z_3)_l-(A_4-Z_4)_m-(CH_2)_n-\text{(oxetanone)}$ |
|---|---|
| 40 | Me–⟨phenyl⟩–⟨cyclohexyl⟩–⟨β-lactone⟩ |
| 41 | MeO–C(=O)–⟨phenyl⟩–⟨cyclohexyl⟩–⟨β-lactone⟩ |
| 42 | F, F₃C, F–⟨phenyl⟩–⟨cyclohexyl⟩–⟨β-lactone⟩ |
| 43 | F₃CO–⟨phenyl⟩–⟨cyclohexyl⟩–⟨β-lactone⟩ |
| 44 | NC–⟨phenyl⟩–⟨phenyl⟩–⟨cyclohexyl⟩–⟨β-lactone⟩ |
| 45 | F,F,F–⟨phenyl⟩–⟨phenyl⟩–⟨cyclohexyl⟩–⟨β-lactone⟩ |
| 46 | F,F–⟨phenyl⟩–⟨phenyl⟩–⟨cyclohexyl⟩–⟨β-lactone⟩ |
| 47 | EtO–⟨phenyl (2,3-diF)⟩–⟨phenyl⟩–⟨cyclohexyl⟩–⟨β-lactone⟩ |
| 48 | C₅H₁₁–⟨phenyl⟩–⟨phenyl⟩–⟨cyclohexyl⟩–⟨β-lactone⟩ |
| 49 | F,F,F–⟨phenyl⟩–⟨phenyl(F)⟩–⟨cyclohexyl⟩–⟨β-lactone⟩ |
| 50 | F,F,F–⟨phenyl⟩–⟨phenyl(2,6-diF)⟩–⟨cyclohexyl⟩–⟨β-lactone⟩ |

-continued
| No. | $R_1\!-\!(\!A_1\!-\!Z_1\!)_j\!(\!A_2\!-\!Z_2\!)_k\!(\!A_3\!-\!Z_3\!)_l\!(\!A_4\!-\!Z_4\!)_m\!(CH_2)_n\!-\!\text{oxetanone}$ |
|---|---|
| 51 | 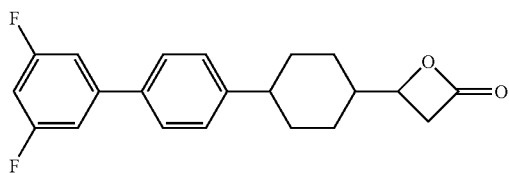 |
| 52 | 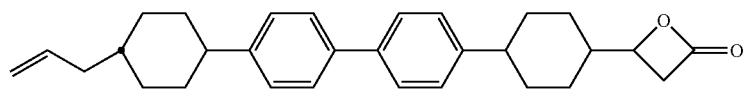 |
| 53 | 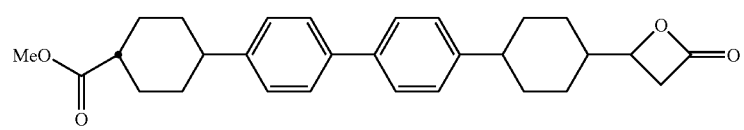 |
| 54 | 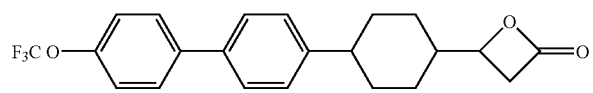 |
| 55 | 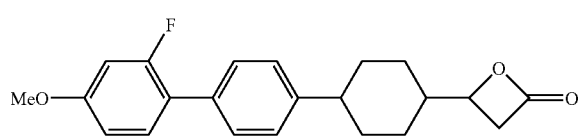 |
| 56 | 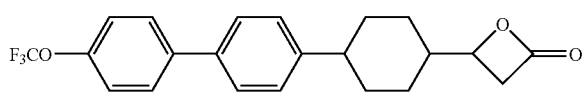 |
| 57 | 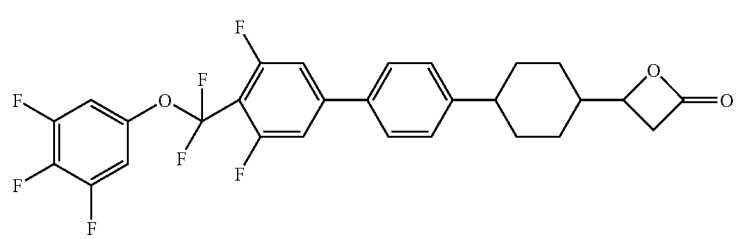 |
| 58 | 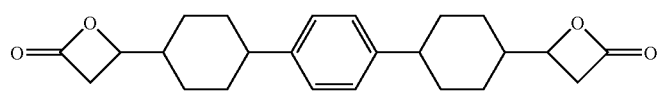 |
| 59 | 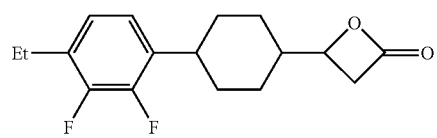 |
| 60 | 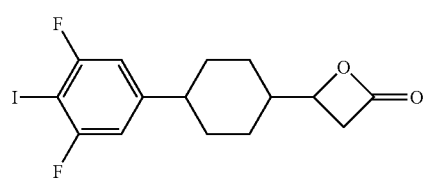 |

-continued

| No. | $R_1-(A_1-Z_1)_j-(A_2-Z_2)_k-(A_3-Z_3)_l-(A_4-Z_4)_m-(CH_2)_n-\text{(oxetanone)}$ |
|---|---|
| 61 | |
| 62 | |
| 63 | |
| 64 | |
| 65 | |
| 66 | |
| 67 | |
| 68 | |
| 69 | |
| 70 | |

-continued
| No. | $R_1-(A_1-Z_1)_j-(A_2-Z_2)_k-(A_3-Z_3)_l-(A_4-Z_4)_m-(CH_2)_n-\overset{O}{\underset{}{\square}}=O$ |
|---|---|
| 71 | 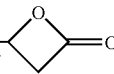 |
| 72 | 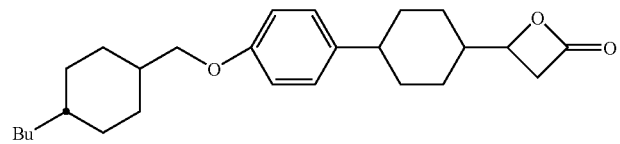 |
| 73 | 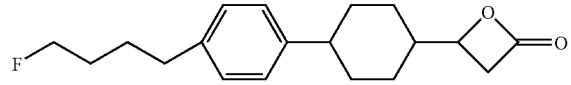 |
| 74 | 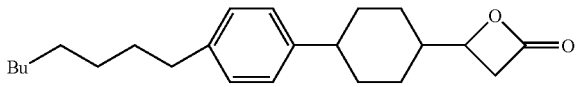 |
| 75 | 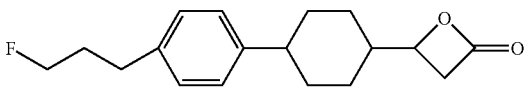 |
| 76 | 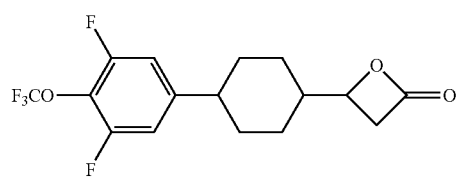 |
|    | 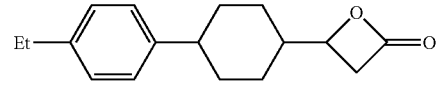 |
| 77 | 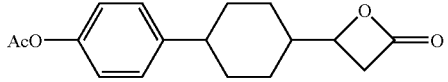 |
| 78 | 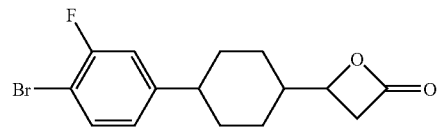 |
| 79 | 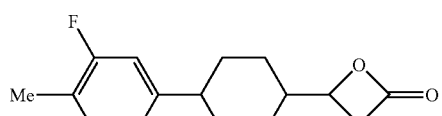 |
| 80 | 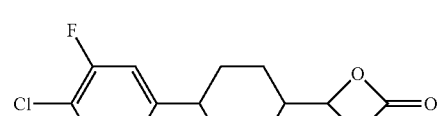 |
| 81 | 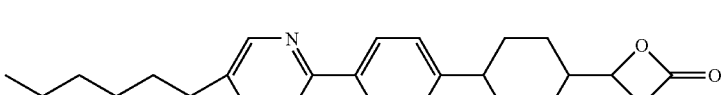 |

| No. | $R_1-(A_1-Z_1)_j-(A_2-Z_2)_k-(A_3-Z_3)_l-(A_4-Z_4)_m-(CH_2)_n-$ [oxetanone] |
|---|---|
| 82 | 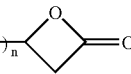 |
| 83 | 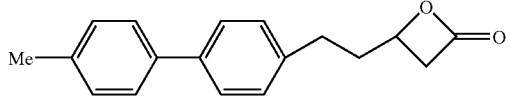 |
| 84 | 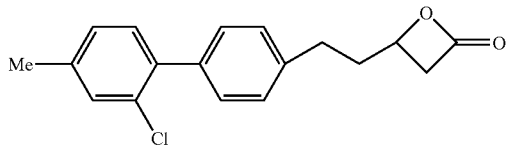 |
| 85 | 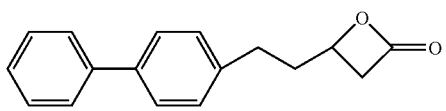 |
| 86 | 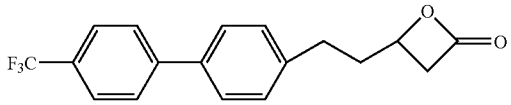 |
| 87 | 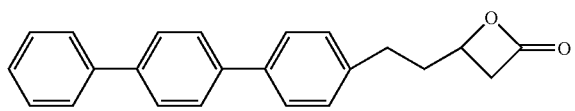 |
| 88 | 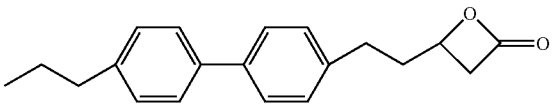 |
| 89 | 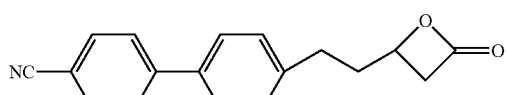 |
| 90 | 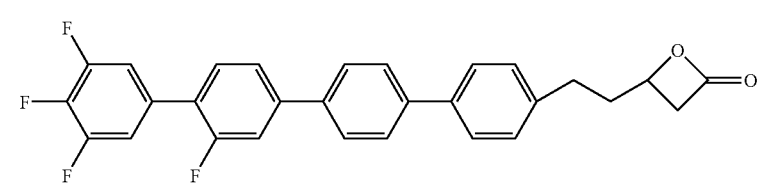 |
| 91 | 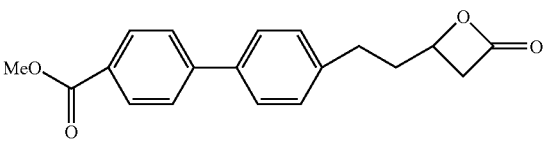 |
| 92 | 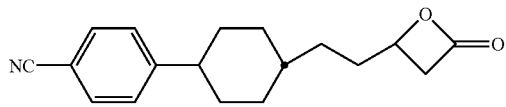 |

-continued

| No. | $R_1-(A_1-Z_1)_j-(A_2-Z_2)_k-(A_3-Z_3)_l-(A_4-Z_4)_m-(CH_2)_n-\text{oxetanone}$ |
|---|---|
| 93 | |
| 94 | |
| 95 | |
| 96 | |
| 98 | |

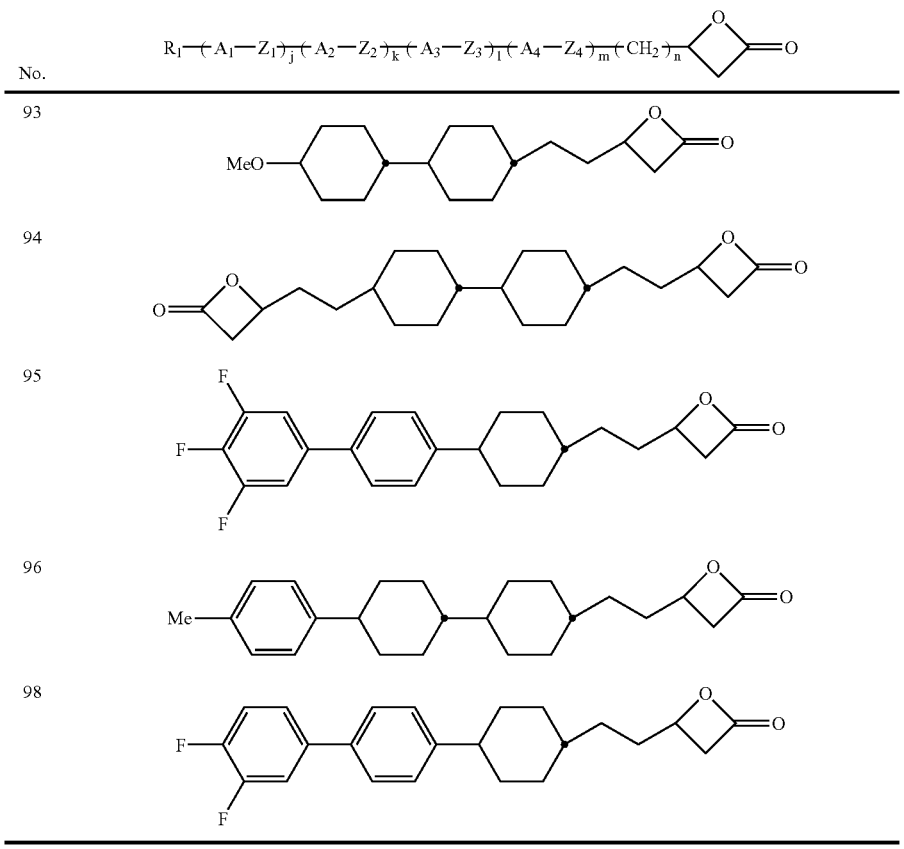

The invention claimed is:

1. A 2-oxetanone derivative represented by the general formula (1):

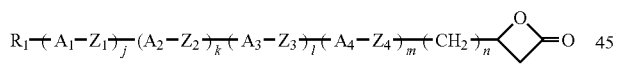

wherein $R_1$ is hydrogen, alkyl having 1 to 20 carbons, halogen, —C≡N, —C≡C—C≡N, —N═C═O or —N═C═S, wherein arbitrary hydrogen may be replaced by halogen in the alkyl;
$A_1$, $A_2$, $A_3$ and $A_4$ are each independently 1,4-cyclohexylene, 1,4-phenylene in which arbitrary hydrogen may be replaced by fluorine, decahydronaphthalen-2,6-diyl, 1,2,3,4-tetrahydronaphthalen-2,6-diyl or naphthalen-2,6-diyl, provided that when $A_1$, $A_2$ and $A_3$ are each 1,4-cyclohexylene, the steric configuration thereof is trans, and when $A_4$ is 1,4-cyclohexylene, the steric configuration thereof may be trans, cis or a mixture of trans and cis;
$Z_1$, $Z_2$, $Z_3$ and $Z_4$ are each independently a single bond, —CH$_2$CH$_2$—, —(CH$_2$)$_4$—, —CH$_2$O— or —OCH$_2$—;
j and k are each independently 0 or 1; l and m are 1; and n is an integer of from 0 to 6.

2. The 2-oxetanone derivative according to claim 1 which is represented by the general formula (1-1):

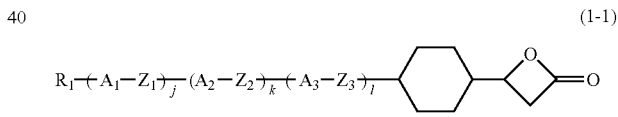

wherein $R_1$ is hydrogen, alkyl having 1 to 15 carbons, halogenated alkyl having 1 to 15 carbons, alkenyl having 2 to 10 carbons, halogen or —C≡N;
$A_1$, $A_2$ and $A_3$ are each independently trans-1,4-cyclohexylene, 1,4-phenylene in which arbitrary hydrogen may be replaced by fluorine, decahydronaphthalen-2,6-diyl, 1,2,3,4-tetrahydronaphthalen-2,6-diyl or naphthalen-2,6-diyl;
$Z_1$, $Z_2$ and $Z_3$ are each independently a single bond, —CH$_2$CH$_2$—, —(CH$_2$)$_4$—, —CH$_2$O— or —OCH$_2$—;
j and k are each independently 0 or 1; and l is 1.

3. A 2-oxetanone derivative represented by the general formula (1-2):

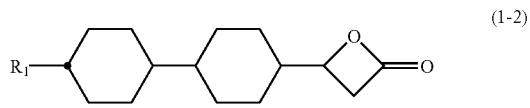

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N.

4. A 2-oxetanone derivative represented by the general formula (1-3):

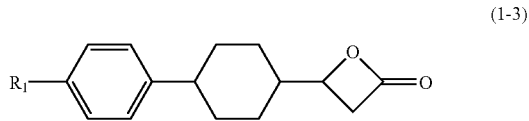

(1-3)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N.

5. A 2-oxetanone derivative represented by the general formula (1-4):

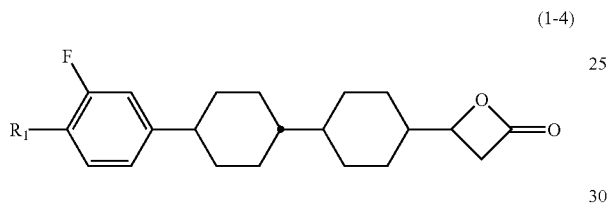

(1-4)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N.

6. A 2-oxetanone derivative represented by the general formula (1-5):

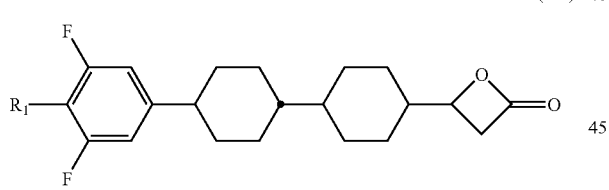

(1-5)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N.

7. A 2-oxetanone derivative represented by the general formula (1-6):

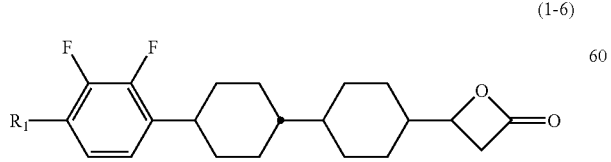

(1-6)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N.

8. A 2-oxetanone derivative represented by the general formula (1-7):

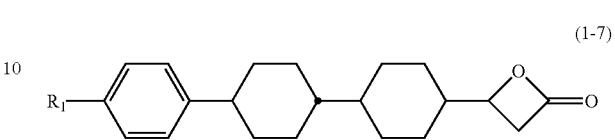

(1-7)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N.

9. A 2-oxetanone derivative represented by the general formula (1-8):

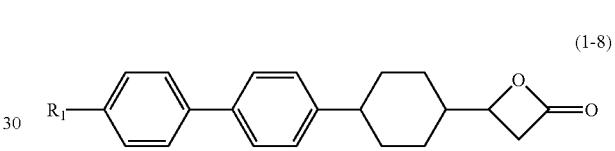

(1-8)

wherein $R_1$ is hydrogen, alkyl having 1 to 15 carbons, halogenated alkyl having 1 to 15 carbons, halogenated alkenyl having 1 to 15 carbons, alkenyl having 2 to 10 carbons, halogen or —C≡N.

10. The 2-oxetanone derivative according to claim 1 which is represented by the general formula (1-9):

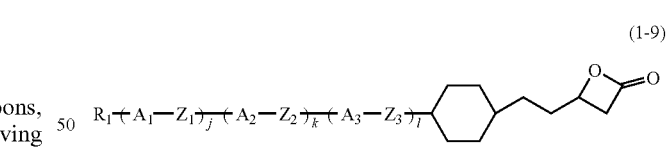

(1-9)

wherein $R_1$ is hydrogen, alkyl having 1 to 15 carbons, halogenated alkyl having 1 to 15 carbons, alkenyl having 2 to 10 carbons, halogen or —C≡N;

$A_1$, $A_2$ and $A_3$ are each independently trans-1,4-cyclohexylene, 1,4-phenylene in which arbitrary hydrogen may be replaced by fluorine, decahydronaphthalen-2,6-diyl, 1,2,3,4-tetrahydronaphthalen-2,6-diyl or naphthalen-2,6-diyl;

$Z_1$, $Z_2$ and $Z_3$ are each independently a single bond, —CH$_2$CH$_2$—, —(CH$_2$)$_4$—, —CH$_2$O— or —OCH$_2$—;

j and k are each independently 0 or 1; and l is 1.

11. A 2-oxetanone derivative represented by the general formula (1-10):

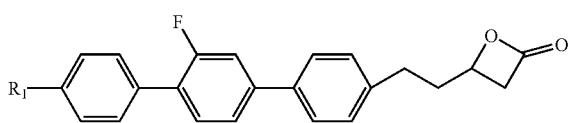

(1-10)

wherein $R_1$ is hydrogen, alkyl having 1 to 15 carbons, alkoxy having 1 to 15 carbons, halogenated alkyl having 1 to 15 carbons, halogenated alkoxy having 1 to 15 carbons, alkenyl having 2 to 10 carbons, halogen or —C≡N.

12. 4-(4-(trans-4-propylcyclohexyl)cyclohexyl)-2-oxetanone, 4-(4-(trans-4-butylcyclohexyl)cyclohexyl)-2-oxetanone or 4-(4-(trans-4-pentylcyclohexyl)cyclohexyl)-2-oxetanone.

* * * * *